(12) United States Patent
Bulkes et al.

(10) Patent No.: US 6,721,386 B2
(45) Date of Patent: Apr. 13, 2004

(54) METHOD AND APPARATUS OF CARDIAC CT IMAGING USING ECG AND MECHANICAL MOTION SIGNALS

(75) Inventors: Cherik Bulkes, Sussex, WI (US); Gopal B. Avinash, New Berlin, WI (US); Tin-su Pan, Brookfield, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 0 days.

(21) Appl. No.: 10/063,066

(22) Filed: Mar. 15, 2002

(65) Prior Publication Data
US 2003/0174804 A1 Sep. 18, 2003

(51) Int. Cl.[7] .................................................. A61B 6/00
(52) U.S. Cl. ............................................. 378/8; 378/95
(58) Field of Search ........................... 378/4, 8, 95, 210

(56) References Cited
U.S. PATENT DOCUMENTS 6,154,516 A * 11/2000 Heuscher et al. ............. 378/15
6,252,924 B1    6/2001 Davantes et al.
6,510,337 B1 *  1/2003 Heuscher et al. ........... 600/428

* cited by examiner

Primary Examiner—David V Bruce
Assistant Examiner—Hoon Song
(74) Attorney, Agent, or Firm—Ziolkowski Patent Solutions Group, LLC; Michael A. Della Penna; Carl B. Horton

(57) ABSTRACT

The present invention is directed to a method and apparatus of cardiac CT imaging. The present invention utilizes ECG signals as well as mechanical motion signals of a cardiac region of a subject to correlate CT data acquired of the subject with the phases of the subject's cardiac region. The present invention contemplates measuring mechanical gatings of the heart by measuring changes in pressure, sound, or blood flow acceleration within the cardiac region. The mechanical gatings are then used with ECG data to correlate acquired imaging data with phases of the cardiac region for subsequent image reconstruction.

23 Claims, 2 Drawing Sheets

METHOD AND APPARATUS OF CARDIAC CT IMAGING USING ECG AND MECHANICAL MOTION SIGNALS

BACKGROUND OF INVENTION

The present invention relates generally to computed tomography imaging and, more particularly, to a method and apparatus of cardiac CT imaging using ECG and mechanical motion signals.

The narrowing or constriction of vessels carrying blood to the heart is a well-known cause of heart attacks and, gone untreated, can lead to sudden death. In such stenotic vessels, it is known that the region immediately downstream from the constriction is characterized by having rapid flow velocities and/or complex flow patterns. In general, narrowing of blood carrying vessels supplying an organ will ultimately lead to compromised function of the organ in question, at best, and organ failure, at worst. Quantitative flow data can readily aid in the diagnosis and management of patients and also help in the basic understanding of disease processes. There are many techniques available for the measurement of blood flow, including imaging based methods using radiographic imaging of contrast agents, both in projection and computed tomography (CT), ultrasound, and nuclear medicine techniques. Radiographic and nuclear medicine techniques often require the use of ionizing radiation and/or contrast agents. Some methods involve making assumptions about the flow characteristics which may not necessarily be true in vivo or require knowledge about the cross-sectional area of the vessel or the flow direction.

CT is one technique of acquiring blood flow and other cardiac data. Typically, in CT imaging systems, an x-ray source emits a fan-shaped beam toward a subject or object, such as a patient or a piece of luggage, for example. Hereinafter, reference to a "subject" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to a data processing system for subsequent image reconstruction by an image reconstructor.

A number of methods have been developed for reconstructing cardiac images. One method incorporates prospective electrocardiogram (ECG) gating with axial slice CT acquisition to reconstruct cardiac images. Another method implements a retrospective ECG-gated CT data acquisition and reconstruction technique using spiral CT to reconstruct cardiac images. A prospective ECG-gated technique with spiral CT data acquisition for imaging only the diastolic phase of the heart is also known. These methods use the ECG data signals alone to find data corresponding to the diastolic and systolic phases of the heart. Further, these known methods have a limited applicability when a pacemaker is used to electrically pace the cardiac cycle of the heart. Moreover, detection of certain heart abnormalities such as premature ventricular contraction is difficult with these known imaging techniques.

It would therefore be desirable to design a method and apparatus of cardiac CT imaging that utilizes both ECG and mechanical motion gating signals for image reconstruction.

BRIEF DESCRIPTION OF INVENTION

The present invention is directed to a method and apparatus of cardiac CT imaging overcoming the aforementioned drawbacks. The present invention implements ECG signals and mechanical motion signals of a cardiac region of a subject for image reconstruction. The present invention acquires mechanical gatings of the heart by utilizing changes in pressure, sound, or blood flow acceleration within the cardiac region. The mechanical gatings are then used with ECG data to correlate acquired imaging data with phases of the cardiac region.

Therefore, in accordance with one aspect of the present invention, a method of reconstructing a cardiac CT image of a subject includes the steps of acquiring a set of electrocardiogram (ECG) signals of a cardiac region of the subject and acquiring a set of mechanical motion signals of the cardiac region. The method further includes correlating the set of ECG signals and the set of mechanical motion signals for determining cardiac phases of the cardiac region of the subject. The method further includes reconstructing an image of the cardiac region from the imaging data.

In accordance with another aspect of the present invention, a cardiac imaging system comprising a radiation emitting imaging device, an ECG monitor, and a cardiac motion sensor is provided. The radiation emitting imaging device is configured to acquire CT data of a subject and reconstruct an image of the subject. The ECG monitor is configured to acquire cardiac data of the subject and the cardiac motion sensor is configured to acquire cardiac data associated with mechanical motion of a cardiac region of the subject. A computer program is further provided to acquire a set of ECG signals of the cardiac region from the ECG monitor, acquire a set of mechanical motion signals of the cardiac region from the cardiac motion sensor, and acquire a set of imaging data from the imaging device. The computer is programmed to compare the set of ECG signals and the set of mechanical motion signals to determine phases of the cardiac region. The computer is then programmed to reconstruct an image of the cardiac region from the set of imaging data using the phases of the cardiac region determined from the set of ECG signals and the set of mechanical motion signals.

In accordance with yet another aspect of the present invention, a computer readable storage medium having a computer program stored thereon is provided. The computer program represents a set of instructions that when executed by one or more computers causes the one or more computers to receive a set of cardiac motion signals from at least one cardiac motion sensor affixed to a subject and receive a set of ECG signals from at least one ECG sensor. The one or more computers also analyze the set of ECG signals and the set of cardiac motion signals to determine phases of a cardiac region of the subject and receive imaging data from a data acquisition system configured to receive imaging data. An image is then reconstructed of the cardiac region of the subject.

In accordance with yet a further aspect of the present invention, an imaging apparatus is provided and includes means for acquiring a set of ECG signals from a patient. The imaging apparatus further includes means for acquiring a set of mechanical motion signals of a cardiac region of the patient as well as means for acquiring imaging data from the patient. The imaging apparatus further comprises means for correlating the set of ECG signals and the set of mechanical motion signals to determine one or more phases of the cardiac region of the patient and means for reconstructing an image of the patient from the imaging data using the correlated set of ECG signals and the set of mechanical motion signals to associate the imaging data with one or more phases of the cardiac region.

Various other features, subjects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable with the detection and conversion of other high frequency electromagnetic energy. Additionally, the present invention will be described with respect to a "third generation" CT imaging system, but is equally applicable with other CT imaging systems.

Figure 1:
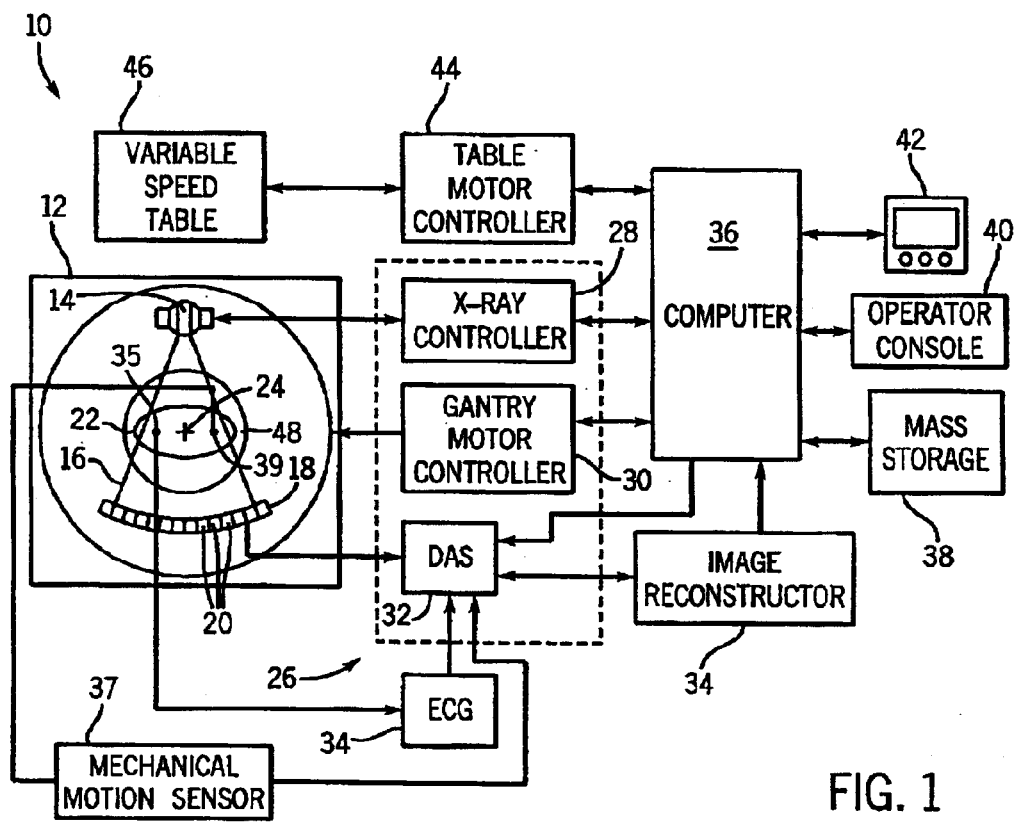
FIG. 1 is a block schematic diagram of a CT imaging system in accordance with one embodiment of the present invention.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. As will be described below, DAS 32 also receives ECG signals from an ECG 33 connected to the subject via leads 35 to acquire cardiac data of the subject 22. DAS 32 also receives mechanical motion data of the subject's cardiac region from a mechanical motion sensor 37 generally connected to the torso region of the subject via leads 39. The computer 36 correlates the ECG and mechanical motion signals to determine the phases of the cardiac region. An image reconstructor 34 receives sampled and digitized x-ray data from DAS 32 and based on the correlation performs high speed reconstruction. The reconstructed image is stored in a mass storage device 38.

Computer 36 also receives commands and scanning parameters from an operator via console 40 that includes a keyboard, a data entry module, or the like. An associated display 42 allows the operator to observe the input data and the reconstructed images or other data from computer 36. The operator supplied commands and parameters are used by computer 36 to provide control signals and information to DAS 32, x-ray controller 28, ECG 33, mechanical motion sensor 37, and gantry motor controller 30. In addition, computer 36 operates a table motor controller 44 which controls a motorized table 46 to position patient 22 and gantry 12. Particularly, table 46 systematically moves patient 22 through a gantry opening 48 for data acquisition.

Figure 2:
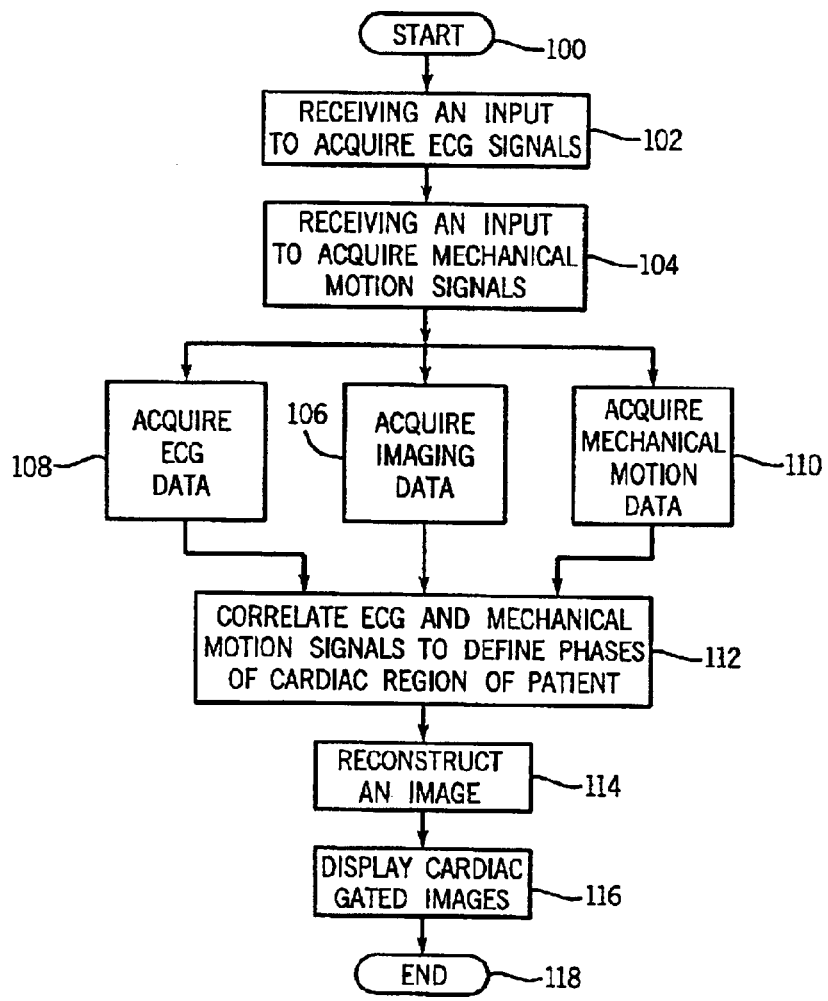
FIG. 2 is a flow chart setting forth the steps of a process for reconstructing cardiac CT images in accordance with the present invention and the acts associated therewith and implemented in the CT imaging system of FIG. 1.

Now referring to FIG. 2, a process for reconstructing cardiac CT images using ECG and mechanical motion gatings is shown. The process begins at 100 with the selection and/or determination of an appropriate scan protocol based on patient parameters. In determining a protocol, in one embodiment, the patient may be instructed to perform several breath-holds to determine typical breath-hold time for this patient. The patient's heart rate may also be acquired and monitored to aid in the selection of the proper imaging protocol. In another embodiment, a pre-scan or pilot-scan may be performed to image the patient's anatomy so the appropriate and desired region of interest is properly imaged. The protocol may be stored in memory of the imaging device, read from a look-up table, or alternatively the operator may prescribe or alter the protocol based on the user's knowledge and experience.

After the appropriate protocol is determined 100, the process continues with receiving an input to acquire ECG signal data at 102 from the patient. The ECG data may be acquired from the patient via leads attached to the patient's torso region. Next, mechanical motion signals of the cardiac region of the medical patient are acquired at 104. The mechanical motion signals may be acquired via sensors affixed to the torso region of the patient. The present invention contemplates several types of sensors to acquire the mechanical gating data. For example, a seismic sensor may be employed to provide a direct measurement of the mechanical motion of the cardiac region. Alternatively, acoustic sensors may be used to detect changes in sound within the cardiac region as evidence of the mechanical motion of the cardiac region. Further, sensors that detect changes in blood flow acceleration may also be utilized to provide direct measurements of the mechanical motion of the cardiac region. It should be noted that the order of steps 102 and 104 may be reversed. That is, the order in which the commands are received is not paramount.

The process continues with the initiation of the CT scan to acquire data whereupon CT imaging data is acquired at 106. Simultaneously therewith, ECG and mechanical motion data are acquired at 108 and 110, respectively. That is, there is a synchronous acquisition of the ECG, mechanical motion, and imaging signals. The ECG and mechanical motion signals are tagged or time-stamped so that the signals may be correlated with the acquired imaging data. The imaging data may also be tagged or time-stamped so that the imaging data corresponding to each phase of the heart is properly identified. At 112, the ECG and mechanical motion signals are correlated to define phases of the heart. Moreover, in one embodiment, x-rays are continually projected to the medical patient throughout the acquisition of ECG and mechanical motion signals so that any phase of the heart may be properly imaged.

At 114, image reconstruction of the cardiac region or heart takes place using the ECG and mechanical motion signals which have been evaluated to determine the phases of the cardiac region and correlated with the imaging data. As indicated previously, the acquired signals are time-stamped which enables the signals to be correlated based on the time acquired. Cardiac gated images are generated and displayed to the operator at 116. An image can be reconstructed of the heart corresponding to a particular point in time and a particular phase of the heart or, alternatively, the reconstructed gated images may be averaged over multiple heart cycles to improve contrast resolution, or for evaluation over time. Upon displaying of the cardiac gated images at 116, the process terminates at 118.

The present invention is particularly applicable for diagnostic 3-D visualization and imaging of the heart and associated vasculature. Cardiac images acquired in accordance with the present invention are particularly useful for quantifying calcifications. Because gated images have fewer artifacts associated with patient motion, gated images are particularly useful for calcification scoring. The aforementioned described process is commonly referred to as retrospective cardiac "gating." However, a more precise term of characterization is retrospective cardiac "correlating" of data which relates to the post-data acquisition processing heretofore described. "Gating" refers to a number of imaging techniques depending upon the particular imaging modality. "Gating" is referenced herein insofar as the term applies to CT imaging and associated techniques and should not be confused with the definition of "gating" as it applies in other modalities, such as magnetic resonance imaging.

Because of the non-invasive nature of CT imaging, the present invention is also particularly useful for cardiac assessment such as coronary angiography. CT imaging may also be used to obtain diagnostic data as to flow-related heart abnormalities. Additionally, the simultaneous usage of both ECG and mechanical gatings assist in avoiding the potential for missing ECG signals when a pacemaker is used to electrically pace the cardiac cycle of the heart. Moreover, simultaneous usage of both ECG and mechanical gatings is helpful in detecting certain abnormalities such as premature ventricular contraction. Mechanical gating may also be used to help identify potential image quality issues associated with the CT scan.

Therefore, in accordance with one embodiment of the present invention, a method of reconstructing a cardiac CT image of a subject includes the steps of acquiring a set of electrocardiogram (ECG) signals of a cardiac region of the subject and acquiring a set of mechanical motion signals of the cardiac region. The method further includes correlating the set of ECG signals and the set of mechanical motion signals for determining cardiac phase of the cardiac region of the subject. The method further includes reconstructing an image of the cardiac region from the imaging data.

In accordance with another embodiment of the present invention, a cardiac imaging system comprising a radiation emitting imaging device, an ECG monitor, and a cardiac motion sensor is provided. The radiation emitting imaging device is configured to acquire CT data of a subject and reconstruct an image of the subject. The ECG monitor is configured to acquire cardiac data of the subject and the cardiac motion sensor is configured to acquire cardiac data associated with mechanical motion of a cardiac region of the subject. A computer program is further provided to acquire a set of ECG signals of the cardiac region from the ECG monitor, acquire a set of mechanical motion signals of the cardiac region from the cardiac motion sensor, and acquire a set of imaging data from the imaging device. The computer is programmed to compare the set of ECG signals and the set of mechanical motion signals to determine phases of the cardiac region. The computer is then programmed to reconstruct an image of the cardiac region from the set of imaging data using the phases of the cardiac region determined from the set of ECG signals and the set of mechanical motion signals.

In accordance with yet another embodiment of the present invention, a computer readable storage medium having a computer program stored thereon is provided. The computer program represents a set of instructions that when executed by one or more computers causes the one or more computers to receive a set of cardiac motion signals from at least one cardiac motion sensor affixed to a scan subject and receive a set of ECG signals from at least one ECG sensor. The one or more computers also analyze the set of ECG signals and the set of cardiac motion signals to determine phases of a cardiac region of the scan subject and receive imaging data from a data acquisition system configured to receive imaging data. An image is then reconstructed of the cardiac region of the subject.

In accordance with yet a further embodiment of the present invention, an imaging apparatus is provided and includes means for acquiring a set of ECG signals from a patient. The imaging apparatus further includes means for acquiring a set of mechanical motion signals of a cardiac region of the patient as well as means for acquiring imaging data from the patient. The imaging apparatus further comprises means for correlating the set of ECG signals and the set of mechanical motion signals to determine one or more phases of the cardiac region of the patient and means for reconstructing an image of the patient from the imaging data using the correlated set of ECG signals and the set of mechanical motion signals to associate the imaging data with one or more phases of the cardiac region.

The present invention has been described in terms of the preferred embodiment, and it is recognized that equivalents, alternatives, and modifications, aside from those expressly stated, are possible and within the scope of the appending claims.

What is claimed is:

1. A method of reconstructing a cardiac CT image of a scan subject, the method comprising the steps of:

acquiring imaging data of a cardiac region of a subject;

acquiring a set of ECG signals and a set of mechanical motion signals of the cardiac region from the subject;

correlating the set of ECG signals and the set of mechanical motion signals to determine a phase of the cardiac region; and reconstructing an image of the cardiac region from the imaging data.

2. The method of claim 1 wherein the step of acquiring the set of mechanical motion signals includes the step of measuring changes in pressure of the cardiac region.

3. The method of claim 1 wherein the step of acquiring the set of mechanical motion signals includes the step of measuring acoustical changes of the cardiac region.

4. The method of claim 1 wherein the step of acquiring the set of mechanical motion signals includes the step of measuring changes in blood acceleration within the cardiac region.

5. The method of claim 1 further comprising the step of acquiring the set of mechanical motion signals with a seismic sensor connected to a torso region of the subject.

6. The method of claim 1 further comprising the step of:
measuring a breathing pattern of the subject during acquisition of CT imaging data; and
predicting potential image quality of the reconstructed image of the cardiac region.

7. A cardiac imaging system comprising:
a radiation emitting imaging device configured to acquire computed tomography data of a scan subject and reconstruct an image of the scan subject from the computed tomography data;
an electrocardiogram (ECG) monitor configured to acquire cardiac data of the scan subject;
a cardiac motion sensor configured to acquire cardiac data associated with mechanical motion of a cardiac region of the scan subject; and
a computer programmed to:
acquire a set of ECG signals of the cardiac region from the ECG monitor;
acquire a set of mechanical motion signals of the cardiac region;
acquire a set of imaging data;
compare the set of ECG signals and the set of mechanical motion signals to determine phases of the cardiac region; and
reconstruct an image of the cardiac region from the set of imaging data using the phases of the cardiac region determined from the set of ECG signals and the set of mechanical motion signals.

8. The system of claim 7 wherein the cardiac motion sensor is further configured to measure changes in pressure within the cardiac region.

9. The system of claim 7 wherein the cardiac motion sensor is further configured to measure acoustical changes within the cardiac region.

10. The system of claim 8 wherein the cardiac motion sensor is further configured to measure changes in acceleration of blood flow in the cardiac region.

11. The system of claim 7 wherein the cardiac motion sensor includes a number of electrodes configured to be applied to a torso region of a patient.

12. A computer readable storage medium having a computer program stored thereon and representing a set of instructions that when executed by one or more computers causes the one or more computers to:
receive a set of cardiac motion signals from at least one cardiac motion sensor affixed to a subject;
receive a set of electrocardiogram signals from at least one electrocardiogram sensor;
receive imaging data from a data acquisition system configured to receive imaging data of the subject;
analyze the set of electrocardiogram signals and the set of cardiac motion signals to determine phases of a cardiac region of the subject; and
reconstruct an image of the cardiac region of the subject from the imaging data using the set of electrocardiogram signals and the set of cardiac motion signals to correlate the imaging data with the phases of the cardiac region of the subject.

13. The computer readable storage medium of claim 12 wherein the set of cardiac motion signals is indicative of changes in pressure within the cardiac region.

14. The computer readable storage medium of claim 12 wherein the set of cardiac motion signals is indicative of changes in sound within the cardiac region.

15. The computer readable storage medium of claim 12 wherein the set of cardiac motion signals is indicative of changes in blood flow acceleration in the cardiac region.

16. The computer readable storage medium of claim 12 wherein the set of instructions further causes the one or more computers to match the set of electrocardiogram signals and the set of cardiac motion signals to collectively identify the phases of the cardiac region.

17. The computer readable storage medium of claim 12 wherein the set of instructions further causes the computer to predict image quality from the set of cardiac motion signals.

18. An imaging apparatus comprising:
means for acquiring a set of electrocardiogram (ECG) signals from a patient;
means for acquiring a set of mechanical motion signals of a cardiac region of the patient;
means for acquiring imaging data from the patient;
means for correlating the set of ECG signals and the set of mechanical motion signals to determine one or more phases of the cardiac region of the patient; and
means for reconstructing an image of the patient from the imaging data using the correlated set of ECG signals and the set of mechanical motion signals to associate the imaging data with the one or more phases of the cardiac region.

19. The imaging apparatus of claim 18 wherein the means for acquiring the set of mechanical motion signals includes means for determining changes in pressure within the cardiac region of the patient.

20. The imaging apparatus of claim 18 wherein the means for acquiring the set of mechanical motion signals includes means for measuring acoustical changes within the cardiac region.

21. The imaging apparatus of claim 18 wherein the means for acquiring the set of mechanical motion signals includes means for determining changes in blood flow acceleration within the cardiac region.

22. The imaging apparatus of claim 18 further comprising means for measuring a breathing pattern of the medical patient during acquisition of the imaging data and means for predicting potential image quality of the reconstructed image of the cardiac region.

23. The imaging apparatus of claim 18 further comprising means for time-stamping the set of mechanical motion signals, the set of ECG signals, and the imaging data.

* * * * *